United States Patent
Shin et al.

(10) Patent No.: US 7,326,389 B2
(45) Date of Patent: Feb. 5, 2008

(54) METHOD OF PRODUCING UNSATURATED ALDEHYDE AND/OR UNSATURATED ACID

(75) Inventors: Hyun Jong Shin, Gwangju (KR); Yeon Shick Yoo, Seoul (KR); Byung Yul Choi, Naju-si (KR); Young Hyun Choi, Naju-si (KR); Young Jin Cho, Naju-si (KR); Duk Ki Kim, Gwangju (KR); Joo Yeon Park, Naju-si (KR); Kwang Ho Park, Daejeon (KR)

(73) Assignee: LG Chem, Ltd. (KR)

( * ) Notice: Subject to any disclaimer, the term of this patent is extended or adjusted under 35 U.S.C. 154(b) by 285 days.

(21) Appl. No.: 11/021,628

(22) Filed: Dec. 23, 2004

(65) Prior Publication Data

US 2005/0209485 A1    Sep. 22, 2005

(30) Foreign Application Priority Data

Dec. 26, 2003    (KR)    ............... 10-2003-0097864

(51) Int. Cl.
*B01J 8/04*    (2006.01)
*B01J 8/02*    (2006.01)
*B01J 19/00*    (2006.01)
*B01J 21/00*    (2006.01)
*F28D 7/00*    (2006.01)

(52) U.S. Cl. .............. 422/198; 422/188; 422/193; 422/201; 422/211; 422/221; 502/100

(58) Field of Classification Search ........... 422/188, 422/190, 193, 198, 201, 211, 221, 213, 216, 422/196, 197, 191, 222; 585/265; 502/100, 502/9, 247
See application file for complete search history.

(56) References Cited

U.S. PATENT DOCUMENTS

| 3,347,798 A | * | 10/1967 | Baer et al. ............ 502/9 |
| 3,622,645 A | * | 11/1971 | Carr et al. ............ 585/265 |
| 4,256,783 A |   | 3/1981 | Takada et al. ............ 422/197 |
| 4,328,130 A | * | 5/1982 | Kyan ............ 502/100 |
| 4,499,203 A | * | 2/1985 | Toulhoat et al. ............ 502/247 |
| 4,615,796 A | * | 10/1986 | Kramer ............ 208/146 |
| 6,040,490 A | * | 3/2000 | Ichioka et al. ............ 585/475 |
| 6,359,184 B1 | * | 3/2002 | Kato et al. ............ 585/321 |
| 6,781,021 B2 | * | 8/2004 | Kato et al. ............ 570/256 |
| 2002/0146358 A1 | * | 10/2002 | Smith et al. ............ 422/188 |
| 2003/0199670 A1 | * | 10/2003 | Grosch et al. ............ 528/425 |

FOREIGN PATENT DOCUMENTS

| JP | 53-030688 |   | 3/1978 |
| JP | 56070090 A | * | 6/1981 |
| JP | 09-241209 |   | 9/1997 |
| JP | 11-080052 |   | 3/1999 |
| JP | 2000-336060 |   | 12/2000 |
| JP | 2001-129384 |   | 5/2001 |
| JP | 2001-137689 |   | 5/2001 |
| JP | 2001-139499 |   | 5/2001 |
| JP | 2003-171340 |   | 6/2003 |
| KR | 1997-0065500 |   | 10/1997 |
| KR | 1020000077433 |   | 12/2000 |

* cited by examiner

*Primary Examiner*—Walter D. Griffin
*Assistant Examiner*—Huy-Tram Nguyen
(74) *Attorney, Agent, or Firm*—Cantor Colburn LLP

(57) ABSTRACT

Disclosed is a shell-and-tube reactor that may be used in a method for producing unsaturated aldehydes and/or unsaturated acids from olefins by means of fixed-bed catalytic partial oxidation. The reactor includes at least one reaction zone of a first-step reaction zone for producing unsaturated aldehydes as a main product and a second-step reaction zone for producing unsaturated acids as a main product, and at least one reaction zone of the reaction zones comprises two or more catalytic layers, each of the catalytic layers being packed with a formed product of catalyst as secondary particles, wherein the secondary particles in each catalytic layer are formed of primary particles of a catalytically active component having a different particle size, and the particle size of primary particles of the catalytically active component is controlled so that it decreases from an inlet of the reactor to an outlet of the reactor. A method for producing unsaturated aldehydes and/or unsaturated fatty acids from olefins using the same reactor is also disclosed. According to the present invention, it is possible to control the temperature efficiently at a hot spot, thereby permitting a catalyst to be used stably, and to produce unsaturated aldehydes and/or unsaturated fatty acids with high yield.

6 Claims, 1 Drawing Sheet

US 7,326,389 B2

METHOD OF PRODUCING UNSATURATED ALDEHYDE AND/OR UNSATURATED ACID

TECHNICAL FIELD

The present invention relates to a method for producing unsaturated aldehydes and/or unsaturated acids from olefins by means of fixed-bed catalytic partial oxidation in a shell-and-tube heat exchange type reactor, as well as to a fixed-bed shell-and-tube heat exchange type reactor used in the above method.

BACKGROUND ART

A process for producing unsaturated aldehydes and/or unsaturated acids from olefins is a typical example of catalytic vapor phase oxidation.

In general, catalytic vapor phase oxidation is implemented as follows. At least one catalyst in the form of granules is packed into reaction tubes, feed gas 1 is supplied to a reactor through the reaction tubes and the feed gas is in contact with the catalyst in the reaction tubes to perform vapor phase oxidation. Reaction heat generated during the reaction is removed by heat transfer with a heat transfer medium, wherein the temperature of the heat transfer medium is maintained at a predetermined temperature. Particularly, the heat transfer medium for heat exchange is provided on the outer surface of the catalytic tubes to perform heat transfer. A reaction mixture 3 containing a desired product is collected via a duct and then sent to a purification step. Generally, catalytic vapor phase oxidation is a highly exothermic reaction. Therefore, it is very important to control the reaction temperature in a specific range and to downsize hot spots in the reaction zone.

To perform the partial oxidation of olefins, a multimetal oxide containing molybdenum and bismuth or vanadium or a mixture thereof is used as a catalyst. Typically, the partial oxidation of olefins may be exemplified by a process for producing (meth)acrolein or (meth)acrylic acid by oxidizing propylene or isobutylene, a process for producing phthalic anhydride by oxidizing naphthalene or ortho-xylene or a process for producing maleic anhydride by partially oxidizing benzene, butylene or butadiene.

Generally, propylene or isobutylene is subjected to two-step catalytic vapor phase partial oxidation to form (meth)acrylic acid as a final product. More particularly, in the first step 10, propylene or isobutylene is oxidized by oxygen, diluted inert gas, water vapor and an optional amount of catalyst to form (meth)acrolein 2 as a main product. In the second step 20, (meth)acrolein obtained from the preceding step is oxidized by oxygen, diluted inert gas, water vapor and an optional amount of catalyst to form (meth)acrylic acid 3. The catalyst used in the first step is an oxidation catalyst based on Mo—Bi, which oxidizes propylene or isobutylene to form (meth)acrolein as a main product. Additionally, a part of (meth)acrolein is further oxidized on the same catalyst to form acrylic acid partially. The catalyst used in the second step is an oxidation catalyst based on Mo—V, which oxidizes (meth)acrolein-containing mixed gas produced in the first step, particularly (meth)acrolein, to form (meth)acrylic acid as a main product.

Reactors for carrying out the above process are realized in such a manner that each of the above two steps are implemented in one system or in two different systems (FIG. 1) (see U.S. Pat. No. 4,256,783).

Meanwhile, many attempts are made to increase productivity of the reactor for producing acrylic acid by modifying the reactor structure, suggesting an optimized catalyst for oxidation or improving the operational conditions.

As mentioned above, vapor phase oxidation of propylene, isobutylene or (meth)acrolein is an exothermic reaction. Therefore, it has a problem in that a hot spot (a point whose temperature is abnormally high or where heat accumulation is relative high) is generated in a catalytic bed in the reactor. Such hot spots show a relatively high temperature compared to other parts of the reactor. Accordingly, in hot spots, complete oxidation proceeds rather than partial oxidation, thereby increasing by-products such as COx, and decreasing the yield of (meth)acrolein or (meth)acrylic acid. Further, the exposure of catalyst to high temperature causes rapid inactivation of catalyst, thereby shortening the lifetime of catalyst. To solve these problems, a method for inhibiting the generation of hot spots and equalizing the availability of catalyst over the whole reactor has been studied to obtain (meth)acrolein or (meth)acrylic acid with high yield and to use the catalyst for a long time. In this regard, many improved catalysts have been continuously suggested.

For example, Japanese Laid-Open Patent Nos. Sho43-24403 and Sho53-30688 disclose a method for packing a catalytic bed by diluting a catalyst with an inactive material in a stepwise manner from the inlet of feed gas to the outlet of feed gas. However, the above method has a problem in that it takes too much time and is very difficult to pack the catalytic bed while varying the dilution ratio with an inactive material from 100% to 0% gradually. In addition, Korean Laid-Open Patent No. 1997-0065500 and Japanese Laid-Open Patent No. Hei9-241209 disclose a method for packing a catalytic bed by controlling the volume of finally formed catalyst (secondary particles) in such a manner that the volume gradually decreases from the inlet to the outlet. However, the above method has problems in that when the finally formed catalyst has a relatively large volume, reaction tubes may be obstructed, and that it is not possible to obtain a desired level of conversion into acrolein and yield of acrylic acid, due to insufficient activity of such large catalyst. Further, Korean Laid-Open Patent No. 2000-77433 and Japanese Laid-Open Patent No. 2000-336060 disclose a method for using multiple kinds of catalysts formed by varying the kind and amount of alkali metals. However, the method has a difficulty in producing catalysts having different activities at a correct ratio because the amount of alkali metal used therein is small. Further, Japanese Laid-Open Patent No. 2003-171340 discloses a method for using multiple kinds of catalysts formed by varying particle diameters of silicon/carbon compounds (carrier). When the catalytic activity is controlled by varying the particles of SiC, particle size of the SiC (used as a carrier) can decreases and however, it is difficult to produce catalysts having different activities by a desired degree, because such decreased carrier particle size bears no relation to the primary particle size of a catalytically active component.

Therefore, there is a continuous need for developing a method for producing unsaturated aldehydes and/or unsaturated fatty acids with high yield and using a catalyst stably, by controlling the temperature of the highest hot spot efficiently.

DISCLOSURE OF THE INVENTION

It is an object of the present invention to provide a method for producing unsaturated aldehydes and/or unsaturated fatty acids with high yield while using a catalyst stably, by controlling the temperature of a hot spot efficiently, wherein the method is performed in at least one reaction zone of a first reaction zone 10 for producing unsaturated aldehydes (for example, (meth) acrolein) as a main product and a second reaction zone 20 for producing unsaturated acids (for example, (meth)acrylic acid) as a main product; at least one reaction zone of the first and the second reaction zones is packed with two or more catalytic layers, thereby dividing the reaction zone(s) into two or more reaction regions; and a formed product (secondary particles) of catalyst packed in each of the catalytic layers is different in particle size of a catalytically active component (primary particles) by controlling the particle size of the catalytically active component (primary particles) in such a manner that it gradually decreases from the reaction zone at the inlet of the reactor to the reaction zone at the outlet of the reactor.

According to an aspect of the present invention, there is provided a method for producing unsaturated aldehydes from olefins by means of fixed-bed catalytic partial oxidation in a shell-and-tube reactor, characterized in that the reactor includes a reaction zone for producing unsaturated aldehydes, comprising two or more catalytic layers, each of the catalytic layers being packed with a formed product of catalyst as secondary particles, wherein the secondary particles in each catalytic layer are formed of primary particles of a catalytically active component having a different particle size, and the particle size of primary particles of the catalytically active component is controlled so that it decreases from the inlet of the reactor to the outlet of the reactor.

According to another aspect of the present invention, there is provided a method for producing unsaturated acids from unsaturated aldehydes by means of fixed-bed catalytic partial oxidation in a shell-and-tube reactor, characterized in that the reactor includes a reaction zone for producing unsaturated acids, comprising two or more catalytic layers, each of the catalytic layers being packed with a formed product of catalyst as secondary particles, wherein the secondary particles in each catalytic layer are formed of primary particles of a catalytically active component having a different particle size, and the particle size of primary particles of the catalytically active component is controlled so that it decreases from the inlet of the reactor to the outlet of the reactor.

According to still another aspect of the present invention, there is provided a shell-and-tube reactor that may be used in a method for producing unsaturated aldehydes and/or unsaturated acids from olefins by means of fixed-bed catalytic partial oxidation, characterized in that the reactor includes at least one reaction zone of a first-step reaction zone for producing unsaturated aldehydes as a main product and a second-step reaction zone for producing unsaturated acids as a main product, and at least one reaction zone of the above reaction zones comprises two or more catalytic layers, each of the catalytic layers being packed with a formed product of catalyst as secondary particles, wherein the secondary particles in each catalytic layer are formed of primary particles of a catalytically active component having a different particle size, and the particle size of primary particles of the catalytically active component is controlled so that it decreases from the inlet of the reactor to the outlet of the reactor.

Hereinafter, the present invention will be explained in detail.

The finally formed product of catalyst packed in the reaction tube of the reactor comprises secondary particles including the aggregate of a plurality of fine unit particles (primary particles) formed of a catalytically active component. For example, the finally formed product of catalyst includes a formed catalyst (secondary particles) obtained by binding a plurality of primary particles formed of a catalytically active component and forming them into a desired shape, and a supported catalyst (secondary particles) obtained by supporting a plurality of primary particles formed of catalytically active component on an inactive carrier having a desired shape.

According to the present invention, particle size of primary particles providing a formed product of catalyst (secondary particle) is controlled instead of controlling particle size of the formed product of catalyst itself. Therefore, it is possible to prevent obstruction of a reaction tube and degradation of catalytic activity caused by controlling particle size of the formed product of catalyst according to the prior art.

Preferably, the olefin, unsaturated aldehyde and unsaturated acid compounds have 3-4 carbon atoms and include propylene or isobutylene, (meth)acrolein and (meth)acrylic acid, respectively.

Preferably, the catalytically active component in the formed product of catalyst used in the first-step reaction zone for producing unsaturated aldehydes as a main product is a metal oxide represented by the following formula 1:

$$Mo_a A_b B_c C_d D_e E_f F_g O_h \qquad \text{[formula 1]}$$

wherein Mo is molybdenum;

A is at least one element selected from the group consisting of Bi and Cr;

B is at least one element selected from the group consisting of Fe, Zn, Mn, Nb and Te;

C is at least one element selected from the group consisting of Co, Rh and Ni;

D is at least one element selected from the group consisting of W, Si, Al, Zr, Ti, Cr, Ag and Sn;

E is at least one element selected from the group consisting of P, Te, As, B, Sb, Sn, Nb, Cr, Mn, Zn, Ce and Pb;

F is at least one element selected from the group consisting of Na, K, Li, Rb, Cs, Ta, Ca, Mg, Sr, Ba and MgO; and each of a, b, c, d, e, f and g represents the atomic ratio of each element, with the proviso that when a=10, b is a number of between 0.01 and 10, c is a number of between 0.01 and 10, d is a number of between 0.0 and 10, e is a number of between 0.0 and 10, f is a number of between 0 and 20, g is a number of between 0 and 10, and h is a number defined depending on the oxidation state of each of the above elements.

Preferably, the catalytically active component in the formed product of catalyst used in the second-step reaction zone for producing unsaturated acids as a main product is a metal oxide represented by the following formula 2:

$$Mo_a W_b V_c A_d B_e C_f O_x \qquad \text{[formula 2]}$$

wherein Mo is molybdenum;

W is tungsten;

V is vanadium;

A is at least one element selected from the group consisting of iron (Fe), copper (Cu), bismuth (Bi), chrome (Cr), cobalt (Co) and manganese (Mn);

B is at least one element selected from the group consisting of tin (Sn), antimony (Sb), nickel (Ni), cesium (Cs) and thallium (Tl);

C is at least one element selected from the group consisting of alkali metals and alkaline earth metals;

O is an oxygen atom; and each of a, b, c, d, e and x represents the atomic ratio of Mo, W, V, A, B and O atoms, with the proviso that when a=10, 0.5≦b≦4, 0.5≦c≦5, 0≦d≦5, 0≦e≦2, 0≦f≦2, and x is a number defined depending on the oxidation state of each of the above elements.

The formed product of catalyst to be packed into a reactor finally may be obtained by forming metal oxide powder (primary particles) through a extrusion process or palletizing process and baking the resultant product. Otherwise, it may be obtained by coating metal oxide (primary particles) in a liquid or powder state onto an inactive carrier and baking the resultant product.

The metal oxide used in the present invention as a catalytically active component (primary particles) may be applied as an aqueous catalyst solution or suspension by stirring and mixing aqueous solution of salts of metals forming the metal oxide. Otherwise, it may be applied as powder by drying the aqueous catalyst solution or suspension.

In producing the aqueous catalyst solution or suspension, there is no particular limitation in salts of metals forming the metal oxide represented by the above formula 1 or 2, in the case of molybdenum, bismuth, vanadium and tungsten. Additionally, in the case of other metal elements, nitrate, acetate, carbonate, organic acid salts, ammonium salts, hydroxides and oxides may be used.

Further, there is no particular limitation in temperature during the baking step in the process for producing the formed product of catalyst according to the present invention. Generally, the formed product may be used after baking it at a temperature lower than 500° C. for 5-20 hours. The baking temperature of the formed products in each of the reaction zones may be the same or different.

According to the present invention, it is possible to control the particle size and particle size distribution of the catalytically active component (primary particles) by optionally carrying out a mechanical pulverization step, or by adjusting the time or strength in the pulverization step, for the aqueous catalyst solution or suspension during the formation thereof or after the formation thereof, or for the powder obtained by drying the aqueous catalyst solution or suspension. It is the most preferable to control the pulverization time.

When the pulverization step is performed in a liquid phase as in the case of aqueous catalyst solution or suspension, a homogenizer or ultrasonic homogenizer may be used. On the other hand, when the pulverization step is performed in a powder state, a ball mill, attrition mill, dynamo mill, etc., may be used. Otherwise, a method and apparatus currently used in controlling particle size distribution may be used. Preferably, the pulverization rate of a homogenizer is controlled to 10-10000 rpm.

When primary particles having a relatively small size are produced, it is preferable to increase the work time and strength of a particle size distribution controller by 1-3 times gradually, compared to primary particles having a relatively large size.

Meanwhile, a hot spot is referred to as a point whose temperature is abnormally high or where heat accumulation is high, in a catalytic bed. In general, in the case of the first-step reaction zone, the highest hot spot is generated at the front part of the first-step reaction zone, enriched with olefins (propylene, isobytylene) as a main reactant and molecular oxygen. Similarly, in the case of the second-step reaction zone, the highest hot spot is generated at the front part of the second-step reaction zone, enriched with unsaturated aldehydes (acrolein) and molecular oxygen. Therefore, the catalytic layer packed with a formed product of catalyst having the largest primary particle size preferably includes the hot spot having the highest temperature. Additionally, the primary particle size of the formed product of catalyst used in the catalytic layer including the highest hot spot is preferably 10-150 microns, more preferably 10-100 microns, and most preferably 10-50 microns.

For example, when two catalytic layers each having a different size of primary particles of catalytically active component are packed into a reaction tube, the relatively large size of primary particles ranges from 10 to 150 microns, preferably from 10 to 100 microns, and more preferably from 10 to 50 microns, while the relative small size of primary particles is 10 microns or less and preferably ranges from 0.01 to 10 microns. In a variant, when three catalytic layers each having a different size of primary particles of catalytically active component are packed into a reaction tube, the largest size of primary particles ranges from 10 to 150 microns, preferably from 10 to 100 microns, and more preferably from 10 to 50 microns, the medium primary particle size ranges from 1 to 10 microns, and the smallest size of primary particles is 1 micron or less and preferably ranges from 0.01 to 1 micron.

Carriers for use in forming-a catalyst by coating a catalytically active component on a carrier include inactive carriers such as alundum, silica-alumina and silicon carbide. When a catalytically active component in a liquid phase or powder state is supported on a carrier, it is preferable that the component is contained in a rotary sugar coater, planetary swing barrel machine, spherudizer, etc. In addition, when a catalyst is formed by using only the catalytically active component powder (primary particles) without any carrier, conventional catalyst forming processes including an extrusion process, palletizing process, etc., may be used. In this case, preferred shapes of the formed product of catalyst include cylindrical shapes and hollow cylindrical shapes. However, when a catalyst is formed by using only the catalytically active component without any carrier, the catalytic activity may be excessively high. Therefore, a formed product of catalyst having a hollow cylindrical shape is more preferable.

There is no particular limitation in shape of a formed product of catalyst and in content of catalytically active component used in the present invention. However, when a catalytically active component is coated on a carrier, it is advisable that a catalytically active component is supported on a spherical carrier in an amount of 20-70% and formed into particles having a size of 3-8 mm in order to facilitate forming and packing of catalyst. On the other hand, when a catalytically active component (primary particles) is directly formed into a formed products of catalyst (secondary particles) without carrier through an extrusion process or pelletizing process, it is advisable that the catalyst has a cylindrical shape having a diameter of 3-8 mm in which a cavity having a diameter of about 0.5-5 mm is perforated so that the content of catalytically active component can be 20-70%.

A plurality of formed products of catalyst having different sizes of primary particles, obtained according to the presence/absence of a pulverization step and conditions in the pulverization step are packed into each of the zones formed by dividing a reaction tube in a reactor in multiple zones. The more the primary particle size of catalytically active component decreases, the more the reactivity increases (while the selectivity and stability decrease). Therefore, when a catalytic layer having a relatively largest size of catalytically active component is packed in the vicinity of the front part of each inlet of the first and the second reaction zones in which the highest hot spot is formed, it is possible to reduce heat generation, to prevent excessive heat accumulation and to inhibit undesired byproduct formation. Additionally, when catalysts having relatively small primary particle sizes are packed sequentially from the next of the hot spot to the rear end of the reaction tube in such a manner that the primary particle size decrease, it is possible to increase the catalytic activity at the rear end of the reaction tube, thereby increasing the overall yield of a desired product and producing a desired final product stably for a long time. More particularly, it is preferable that a catalyst having the largest primary particle size is used in the vicinity of the hot spot and a catalyst having a relatively small primary particle size is used in a part following the vicinity of the hot spot. According to the present invention, the primary particle size of a catalytically active component decreases gradually from the inlet of the reactor to the outlet of the reactor. In other words, the catalytic activity increases gradually from the inlet to the outlet.

Theoretically, when the number of reaction zones increases, the reaction zones being divided through the use of different catalytic layers in the first step and the second step depending on the exothermic temperature distribution of the reactor, it is possible to control the reaction heat more easily. However, it is not possible to increase the number of reaction zones infinitely when viewed from a commercial point of view. Therefore, in order to satisfy the effect of the present invention to a desired degree, it is preferable to use two or three reaction zones. Meanwhile, each catalytic layer may be packed to any height capable of controlling the heat generation of the reactor efficiently. The packing height of the catalytic layer having the largest primary particle size of catalytically active component preferably includes the highest hot spot. More particularly, the above-mentioned packing height, starting from the inlet, is 10-50%, preferably 10-30% of the total height of the catalytic bed.

Since methods for packing a catalyst into a commercial reactor are generally known, a packing method suitable for a given reactor can be used. Additionally, it is preferable to pack a predetermined amount of catalyst separately for each reaction tube.

For example, in order to perform oxidation in a reactor according to the present invention, a feed gas 1 including 1-10 volume % of a feed compound such as propylene, 1-15 volume % of oxygen, 5-60 volume % of water vapor and 20-80 volume % of an inert gas is introduced onto a catalyst at a temperature ranging from 200° C. to 350° C., under a pressure of between atmospheric pressure and 3 atm, at a space velocity of 500-4000 hr$^{-1}$ (STP).

MODE FOR CARRYING OUT THE INVENTION

Figure 1:
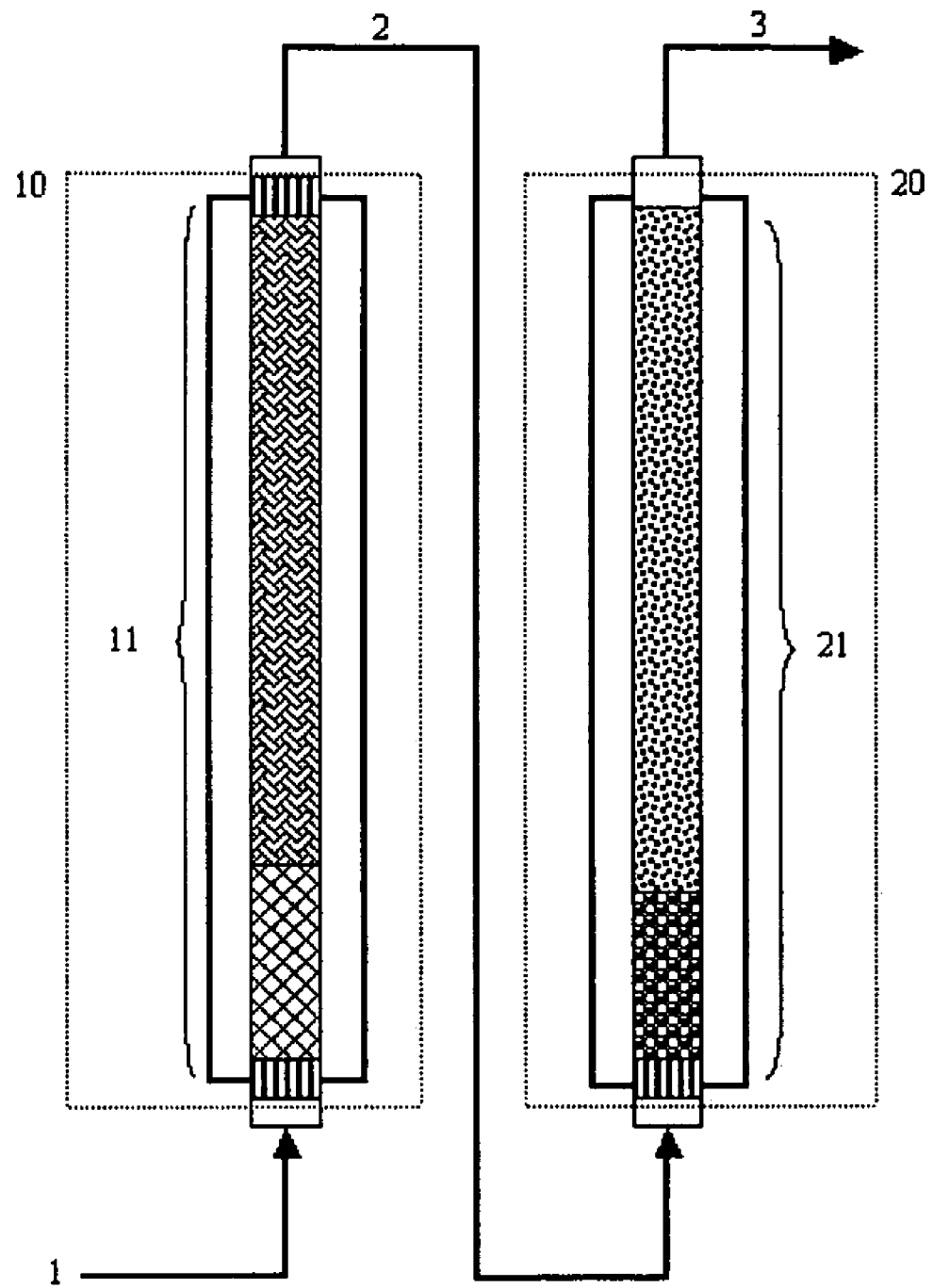
FIG. 1 is a schematic view showing the structure of a pilot reactor, wherein the first step and the second step of reactions are performed individually in a different reactor, each reactor comprising one catalytic tube, and the structure of a catalytic bed disposed inside of the catalytic tube.

Reference will now be made in detail to the preferred embodiments of the present invention. It is to be understood that the following examples are illustrative only and the present invention is not limited thereto.

EXAMPLE 1

(Preparation of Catalyst 1)

To a 50 L glass reactor equipped with a conventional branch type agitator and homogenizer, 40 L of distilled water was introduced and then heated. At 90° C., 10,000 g of ammonium molybdate was dissolved therein to form solution (1). To 2500 ml of distilled water, 6600 g of cobalt nitrate, 4120 g of bismuth nitrate, 2750 g of iron nitrate, 185 g of cerium nitrate and 28.63 g of potassium nitrate were added and then mixed thoroughly to form solution (2). Solution (1) was mixed with solution (2) slowly by using the homogenizer. After both solutions were completely mixed, the homogenizer was further operated for 30 minutes continuously. The resultant suspension was collected and the particle size distribution of precipitate was determined. The precipitate comprised 90% or more of particles having a size of 10-50 microns with no particles having a size greater than 100 microns.

After the suspension obtained as described above was dried for 12 hours or more, the resultant powder was pulverized and formed into ring-shaped pellets having an inner diameter of 2 mm, outer diameter of 6 mm and a length of 6 mm. The pellets were baked at 450° C. under air for 5 hours and then checked for catalytic activity.

The resultant catalytically active component had the composition of: $Mo_{10}Bi_{1.5}Fe_{1.2}Co_4K_{0.05}Ce_{0.1}$ (Catalyst 1), excluding oxygen.

(Preparation of Catalyst 2)

The process described in the above Preparation of Catalyst 1 was repeated to provide Catalyst 2, except that the homogenizer was used for 60 minutes. The resultant suspension was collected and the particle size distribution of precipitate was determined. The precipitate comprised 93% or more of particles having a size of 10 microns or less. The resultant catalytically active component had the composition of: $Mo_{10}Bi_{1.5}Fe_{1.2}Co_4K_{0.05}Ce_{0.1}$ (Catalyst 2), excluding oxygen.

(Oxidation)

To a stainless steel reactor having an inner diameter of 1 inch, Catalyst 1 was packed to the height of 300 mm and Catalyst 2 was packed to the height of 600 mm, from the inlet of the reaction gas toward the outlet. Then, a mixed gas containing 8 volume % of propylene, 14 volume % of oxygen, 18 volume % of water vapor and 60 volume % of inert gas was subjected to oxidation at the space velocity of 1600 hr$^{-1}$ and at the reaction temperature of 280° C. The results are shown in the following Table 2.

COMPARATIVE EXAMPLE 1

Oxidation in Example 1 was repeated, except that Catalyst 1 was packed alone to the height of 900 mm instead of using Catalyst 1 together with Catalyst 2. The results are shown in the following Table 2.

COMPARATIVE EXAMPLE 2

Oxidation in Example 1 was repeated, except that Catalyst 2 was packed alone to the height of 900 mm instead-of using Catalyst 1 together with Catalyst 2. The results are shown in the following Table 2.

COMPARATIVE EXAMPLE 3

(Preparation of Catalyst 3)

The process described in the above Preparation of Catalyst 1 was repeated to provide Catalyst 3, except that the homogenizer was not used. The resultant suspension was collected and the particle size distribution of precipitate was determined. The precipitate comprised no particles having a size of 100 microns or less. The resultant catalytically active component had the composition of: $Mo_{10}Bi_{1.5}Fe_{1.2}Co_4K_{0.05}Ce_{0.1}$ (Catalyst 3), excluding oxygen.

(Oxidation)

Oxidation in Example 1 was repeated, except that Catalyst 3 was packed alone to the height of 900 mm instead of using Catalyst 1 together with Catalyst 2. The results are shown in the following Table 2.

EXAMPLE 2

(Preparation of Catalyst 4)

To a 50 L glass reactor equipped with a conventional branch type agitator and homogenizer, 30 L of distilled water was introduced and then heated. After reaching the boiling point, 2960 g of ammonium paratungstate, 10000 g of ammonium molybdate and 2320 g of ammonium metavanadate were introduced thereto, in turn. Then, the mixture was heated so as to maintain the boiling state, while agitating the mixture until it was completely dissolved. Next, an aqueous solution containing 1370 g of copper nitrate, 1650 g of nickel nitrate and 960 g of strontium nitrate in 2.6 L of water was added to the mixed aqueous solution containing the above three kinds of ammonium salts, while the homogenizer was rotated at 4000 rpm. After both aqueous solutions were completely mixed, the homogenizer was further operated for 30 minutes. The resultant suspension was collected and the particle size distribution of precipitate was determined. The precipitate comprised 80% or more of particles having a size of 10-50 microns with no particles having a size greater than 100 microns.

The suspension obtained as described above was sprayed onto a silica-alumina carrier having a diameter of 5 mm disposed in a sugar coater through a spray nozzle to coat the carrier. At the same time, the coated carrier was dried with hot air at 100° C. to obtain a catalyst supported on a carrier. The resultant catalyst supported on a carrier was baked at 450° C. for 5 hours under air flow to provide a finally formed product of catalyst (Catalyst 4). After baking, the amount of the coated catalyst powder was 30 wt % based on the total weight of the carrier and the catalyst powder. The resultant catalytically active component had the composition of: $Mo_{10}W_2V_{3.5}Cu_1Ni_1Sr_{0.8}$, excluding oxygen.

(Preparation of Catalyst 5)

The process described in the above Preparation of Catalyst 4 was repeated to provide Catalyst 5, except that the homogenizer was used for 1 hour. The resultant suspension was collected and the particle size distribution of precipitate was determined. The precipitate comprised 80% or more of particles having a size of 10 microns or less. The resultant catalytically active component had the composition of: $Mo_{10}W_2V_{3.5}Cu_1Ni_1Sr_{0.8}$, excluding oxygen.

(Oxidation)

To a stainless steel reactor having an inner diameter of 1 inch, Catalyst 4 was packed to the height of 1000 mm and Catalyst 5 was packed to the height of 2000 mm, when viewed from the inlet of the reaction gas toward the outlet. Then, a mixed gas containing 7 volume % of acrolein, 13 volume % of oxygen, 20 volume % of water vapor and 60 volume % of inert gas was subjected to oxidation at the space velocity of 1800 $hr^{-1}$ and at the reaction temperature of 250° C.

COMPARATIVE EXAMPLE 4

Oxidation in Example 2 was repeated, except that Catalyst 4 was packed alone to the height of 3000 mm.

COMPARATIVE EXAMPLE 5

Oxidation in Example 2 was repeated, except that Catalyst 5 was packed alone to the height of 3000 mm.

COMPARATIVE EXAMPLE 6

(Preparation of Catalyst 6)

The process described in the above Preparation of Catalyst 4 in Example 2 was repeated to provide Catalyst 6, except that the homogenizer was not used. The resultant suspension was collected and the particle size distribution of precipitate was determined. The precipitate comprised no particles having a size of 100 microns or less. The resultant catalytically active component had the composition of: $Mo_{10}W_2V_{3.5}Cu_1Ni_1Sr_{0.8}$, excluding oxygen.

(Oxidation)

Oxidation in Example 2 was repeated, except that Catalyst 6 was packed alone to the height of 3000 mm instead of using Catalyst 4 together with Catalyst 5.

EXAMPLE 3

(Preparation of Catalyst 7)

To a 50 L glass reactor equipped with a conventional branch type agitator and homogenizer, 30 L of distilled water was introduced and then heated. After reaching the boiling point, 2960 g of ammonium paratungstate, 10000 g of ammonium molybdate and 2320 g of ammonium metavanadate were introduced thereto, in turn. Then, the mixture was heated so as to maintain the boiling state, while agitating the mixture until it was completely dissolved. Next, an aqueous solution containing 2740 g of copper nitrate, 2400 g of niobium nitrate and 960 g of strontium nitrate in 2.6 L of water was added to the mixed aqueous solution containing the above three kinds of ammonium salts, while the homogenizer was rotated at 4000 rpm. After both aqueous solutions were completely mixed, the homogenizer was further operated for 30 minutes. The resultant suspension was collected and the particle size distribution of precipitate was determined. The precipitate comprised 80% or more of particles having a size of 10-50 microns with no particles having a size greater than 100 microns.

After the suspension obtained as described above was dried for 12 hours or more, the resultant powder was pulverized and formed into ring-shaped pellets having an inner diameter of 4 mm, outer diameter of 6 mm and a length of 6 mm. The pellets were baked at 450° C. under air for 5 hours to provide a finally formed product of catalyst (Catalyst 7). The resultant catalytically active component had the composition of: $Mo_{10}W_2Nb_{2.5}V_{3.5}CU_2Sr_{0.8}$, excluding oxygen.

(Preparation of Catalyst 8)

The process described in the above Preparation of Catalyst 7 was repeated to provide Catalyst 8, except that the homogenizer was used for 1 hour. The resultant suspension was collected and the particle size distribution of precipitate was determined. The precipitate comprised 80% or more of particles having a size of 10 microns or less. The resultant catalytically active component had the composition of: $Mo_{10}W_2Nb_{2.5}V_{3.5}Cu_2Sr_{0.8}$, excluding oxygen.

(Oxidation)

To a stainless steel reactor having an inner diameter of 1 inch, Catalyst 7 was packed to the height of 300 mm and Catalyst 8 was packed to the height of 600 mm, when viewed from the inlet of the reaction gas toward the outlet. Then, a mixed gas containing 7 volume % of acrolein, 13 volume % of oxygen, 20 volume % of water vapor and 60 volume % of inert gas was subjected to oxidation at the space velocity of 1800 hr$^{-1}$ and at the reaction temperature of 250° C.

COMPARATIVE EXAMPLE 7

Oxidation in Example 3 was repeated, except that Catalyst 7 was packed alone to the height of 900 mm.

COMPARATIVE EXAMPLE 8

Oxidation in Example 3 was repeated, except that Catalyst 8 was packed alone to the height of 900 mm.

COMPARATIVE EXAMPLE 9

(Preparation of Catalyst 9)

The process described in the above Preparation of Catalyst 7 in Example 3 was repeated to provide Catalyst 6, except that the homogenizer was not used. The resultant suspension was collected and the particle size distribution of precipitate was determined. The precipitate comprised no particles having a size of 100 microns or less. The resultant catalytically active component had the composition of: $Mo_{10}W_2Nb_{2.5}V_{3.5}Cu_2Sr_{0.8}$, excluding oxygen.

(Oxidation)

Oxidation in Example 3 was repeated, except that Catalyst 9 was packed alone to the height of 900 mm instead of using Catalyst 7 together with Catalyst 8.

The following Table 1 shows the particle size and particle size distribution of primary particles formed of catalytically active component in the finally formed product of catalyst obtained from the above Examples and Comparative Examples.

TABLE 1

| COMPOSITION | HOMOGENIZER WORK TIME (min) | PARTICLE SIZE AND PARTICLES SIZE DISTRIBUTION OF CATALYTICALLY ACITVE COMPONENT |
|---|---|---|
| Catalyst 1  $Mo_{10}Bi_{1.5}Fe_{1.2}Co_4K_{0.05}Ce_{0.1}$ | 30 | 10~50 microns (90% or more) |
| Catalyst 2  $Mo_{10}Bi_{1.5}Fe_{1.2}Co_4K_{0.05}Ce_{0.1}$ | 60 | 10 microns or less (93% or more) |
| Catalyst 3  $Mo_{10}Bi_{1.5}Fe_{1.2}Co_4K_{0.05}Ce_{0.1}$ | 0 | 100 microns or more |
| Catalyst 4  $Mo_{10}W_2V_{3.5}Cu_1Ni_1Sr_{0.8}$ | 30 | 10~50 microns (80% or more) |
| Catalyst 5  $Mo_{10}W_2V_{3.5}Cu_1Ni_1Sr_{0.8}$ | 60 | 10 microns or less (80% or more) |
| Catalyst 6  $Mo_{10}W_2V_{3.5}Cu_1Ni_1Sr_{0.8}$ | 0 | 100 microns or more |
| Catalyst 7  $Mo_{10}W_2Nb_{2.5}V_{3.5}Cu_2Sr_{0.8}$ | 30 | 10~50 microns (80% or more) |
| Catalyst 8  $Mo_{10}W_2Nb_{2.5}V_{3.5}Cu_2Sr_{0.8}$ | 60 | 10 microns or less (80% or more) |
| Catalyst 9  $Mo_{10}W_2Nb_{2.5}V_{3.5}Cu_2Sr_{0.8}$ | 0 | 100 microns or more |

The following Table 2 shows the results obtained from the oxidation of propylene performed by using each of the reactors packed with the catalysts according to Example 1 and Comparative Examples 1, 2 and 3. Further, the following Table 3 shows the results obtained from the oxidation of acrolein performed by using the catalysts according to Examples 2 and 3 and Comparative Examples 4-9.

In Tables 2 and 3, the reactant (propylene or acrolein) conversion ratio, selectivity and yield are calculated based on the following mathematical formulae 1-6.

propylene conversion ratio(%)=[moles of reacted propylene/moles of supplied propylene]×100     [mathematical formula 1]

selectivity(%) to acrolein+acrylic acid=[moles of produced acrolein and acrylic acid/moles of reacted propylene]×100     [mathematical formula 2]

yield(%) of acrolein+acrylic acid=[moles of produced acrolein and acrylic acid/moles of supplied propylene]×100     [mathematical formula 3]

acrolein conversion ratio(%)=[moles of reacted acrolein/moles of supplied acrolein]×100     [mathematical formula 4]

selectivity(%) to acrylic acid=[moles of produced acrylic acid/moles of reacted acrolein]×100     [mathematical formula 5]

yield(%) of acrylic acid=[moles of produced acrylic acid/moles of supplied acrolein]×100.[mathematical formula 6]

TABLE 2

| | CATALYST | REACTION TEMPERATURE (° C.) | HIGHEST HOT SPOT (° C.) | *C$_3$" CONVERSION RATIO (%) | *AA + ACR SELECTIVITY (%) | *AA + ACR YIELD (%) |
|---|---|---|---|---|---|---|
| Ex. 1 | Catalyst 1 (300 mm) + | 280 (initial time) | 340 | 97.3 | 96.1 | 93.5 |
| | Catalyst 2 (600 mm) | 280 (after 168 h) | 340 | 97.2 | 96.0 | 93.3 |
| Comp. Ex. 1 | Catalyst 1 (900 mm) | 280 | 340 | 94.0 | 95.2 | 89.5 |
| Comp. Ex. 2 | Catalyst 2 (900 mm) | 270 | 359 | 97.5 | 92.4 | 90.1 |

TABLE 2-continued

| | CATALYST | REACTION TEMPERATURE (° C.) | HIGHEST HOT SPOT (° C.) | *C₃" CONVERSION RATIO (%) | *AA + ACR SELECTIVITY (%) | *AA + ACR YIELD (%) |
|---|---|---|---|---|---|---|
| Comp. Ex. 3 | Catalyst 3 (900 mm) | 280 | 307 | 93.2 | 95.0 | 88.5 |

*$C_3$" = propylene, ACR = acrolein, AA = acrylic acid

TABLE 3

| | CATALYST | REACTION TEMPERATURE (° C.) | HIGHEST HOT SPOT (° C.) | ACROLEIN CONVERSION RATIO (%) | ACRYLIC ACID SELECTIVITY (%) | ACRYLIC ACID YIELD (%) |
|---|---|---|---|---|---|---|
| Ex. 2 | Catalyst 4 (1000 mm) + | 250 (initial time) | 310 | 98.9 | 97.3 | 96.2 |
| | Catalyst 5 (2000 mm) | 260 (after 4000 h) | 318 | 98.7 | 97.4 | 96.1 |
| Comp. Ex. 4 | Catalyst 4 (3000 mm) | 250 | 310 | 95.7 | 96.7 | 92.5 |
| Comp. Ex. 5 | Catalyst 5 (3000 mm) | 240 | 339 | 99.3 | 93.9 | 93.2 |
| Comp. Ex. 6 | Catalyst 6 (3000 mm) | 250 | 307 | 94.8 | 96.7 | 91.7 |
| Ex. 3 | Catalyst 7 (300 mm) + | 250 (initial time) | 314 | 99.3 | 96.1 | 95.4 |
| | Catalyst 8 (600 mm) | 250 (after 168 h) | 314 | 99.2 | 96.2 | 95.4 |
| Comp. Ex. 7 | Catalyst 7 (900 mm) | 250 | 314 | 96.2 | 95.4 | 91.8 |
| Comp. Ex. 8 | Catalyst 8 (900 mm) | 240 | 344 | 99.6 | 92.7 | 92.3 |
| Comp. Ex. 9 | Catalyst 9 (900 mm) | 250 | 311 | 95.4 | 95.2 | 90.8 |

As shown in Tables 2 and 3, Examples 1, 2 and 3 using two kinds of formed catalysts having different primary particle size of catalytically active component to perform oxidation provide excellent reactant (propylene or acrolein) conversion ratio and selectivity and yield to a desired product compared to Comparative Examples 1-9 using a formed catalyst having the same primary particle size of catalytically active component, respectively.

INDUSTRIAL APPLICABILITY

As can be seen from the foregoing, according to the present invention using two kinds of catalysts having a different particle size of catalytically active component, it is possible to efficiently control the temperature of the highest hot spot in a reactor, to use a catalyst stably and to produce unsaturated aldehydes and/or unsaturated fatty acids with high yield. Additionally, it is possible to produce unsaturated aldehydes and/or unsaturated fatty acids in a stable manner even under a high concentration of starting materials, high space velocity and high load, thereby improving the productivity significantly.

The invention claimed is:

1. A shell-and-tube reactor that may be used in a method for producing unsaturated aldehydes and/or unsaturated acids from olefins by means of fixed-bed catalytic partial oxidation,
   wherein the reactor includes at least one reaction zone of a first-step reaction zone for producing unsaturated aldehydes as a main product and a second-step reaction zone for producing unsaturated acids as a main product, and at least one reaction zone of the reaction zones comprises two or more catalytic layers, each of the catalytic layers being packed with a formed product of catalyst as secondary particles; and
   wherein the secondary particles in each catalytic layer are formed of primary particles of a catalytically active component having a different particle size, and the particle size of primary particles of the catalytically active component is controlled so that it decreases from an inlet of the reactor to an outlet of the reactor.

2. The reactor according to claim 1, wherein the catalytically active component is obtained by agitating and mixing a solution of salts of metals forming a metal oxide to form an aqueous catalyst solution or suspension; and carrying out a pulverization step during or after the formation of the aqueous catalyst solution or suspension in order to control the primary particle size of the catalytically active component.

3. The reactor according to claim 1, wherein the catalytically active component is obtained by agitating and mixing a solution of salts of metals forming a metal oxide to form an aqueous catalyst solution or suspension; and drying the aqueous catalyst solution or suspension to obtain powder and pulverizing the powder to control the primary particle size of the catalytically active component.

4. The reactor according to claim 1, wherein the formed product of catalyst is a formed catalyst obtained by binding a plurality of primary particles formed of a catalytically active component and forming them into a desired shape, or a supported catalyst obtained by supporting a plurality of primary particles formed of a catalytically active component on an inactive carrier having a desired shape.

5. The reactor according to claim 1, wherein the catalytic bed is packed in two catalytic layers, including a first layer having a catalytically active component with a primary particle size of 10-150 microns and a second layer having a catalytically active component with a primary particle size of 10 microns or less.

6. The reactor according to claim 1, wherein the catalytic bed is packed in three catalytic layers, including a first layer having a catalytically active component with a primary particle size of 10-150 microns, a second layer having a catalytically active component with a primary particle size of 1-10 microns, and a third layer having a catalytically active component with a primary particle size of 1 micron or less.

* * * * *